(12) United States Patent
Perez

(10) Patent No.: US 8,506,898 B2
(45) Date of Patent: Aug. 13, 2013

(54) SPECIMEN GATHERING DEVICE AND METHOD OF USE

(75) Inventor: Vincent I. Perez, Indianapolis, IN (US)

(73) Assignee: Perez Forensic Strategies, LLC, Indianapolis, IN (US)

( * ) Notice: Subject to any disclaimer, the term of this patent is extended or adjusted under 35 U.S.C. 154(b) by 668 days.

(21) Appl. No.: 12/174,213

(22) Filed: Jul. 16, 2008

(65) Prior Publication Data

US 2009/0023219 A1 Jan. 22, 2009

Related U.S. Application Data

(60) Provisional application No. 60/959,703, filed on Jul. 16, 2007.

(51) Int. Cl.
*A61L 2/00* (2006.01)
*A61L 9/00* (2006.01)

(52) U.S. Cl.
USPC .............. 422/292; 436/18; 436/63; 401/118; 401/119; 604/1; 600/572; 600/573

(58) Field of Classification Search
None
See application file for complete search history.

(56) References Cited

U.S. PATENT DOCUMENTS

| | | | |
|---|---|---|---|
| 3,995,618 A * | 12/1976 | Kingsley et al. | 600/572 |
| 4,211,323 A | 7/1980 | Olsen | |
| 4,294,582 A | 10/1981 | Naslund | |
| 4,707,450 A | 11/1987 | Nason | |
| 5,186,900 A * | 2/1993 | Jensen et al. | 422/104 |
| 5,256,537 A * | 10/1993 | Phillips et al. | 435/7.1 |
| 5,266,266 A | 11/1993 | Nason | |
| 5,543,115 A | 8/1996 | Karakawa | |
| 5,665,094 A | 9/1997 | Goldenberg | |
| 6,085,907 A * | 7/2000 | Hochmeister et al. | 206/569 |
| 6,171,259 B1 | 1/2001 | Fisher | |
| 6,248,294 B1 | 6/2001 | Nason | |
| 7,022,289 B1 | 4/2006 | Schlein | |
| 7,098,040 B2 | 8/2006 | Kaylor et al. | |
| 7,132,249 B1 * | 11/2006 | Salter et al. | 435/8 |
| 2004/0161855 A1 | 8/2004 | Kvasnik et al. | |
| 2005/0252820 A1 | 11/2005 | Sanchez-Felix et al. | |
| 2006/0078988 A1 | 4/2006 | Eversdijk | |
| 2006/0147249 A1 | 7/2006 | Fuller | |
| 2006/0223071 A1 | 10/2006 | Wisniewski et al. | |

FOREIGN PATENT DOCUMENTS

WO 9614570 5/1996

OTHER PUBLICATIONS

UK Examination Report under Section 18(3) for Patent Application No. GB1002437.0, claiming priority to U.S. Appl. No. 60/959,703; date of report May 31, 2011; receipt date of report Jul. 22, 2011.
International Search Report and Written Opinion for International Application No. PCT/US2008/070175, claiming priority to U.S. Appl. No. 60/959,703; date of completion Jan. 6, 2009; date of mailing Feb. 10, 2009.

* cited by examiner

*Primary Examiner* — Dirk Bass
(74) *Attorney, Agent, or Firm* — Barnes & Thornburg LLP

(57) ABSTRACT

A kit is provided for gathering biological specimens. The kit generally comprises a self-contained specimen gathering device including a protective housing and a preservation solution. Also provided is a method of gathering specimens and a holistic method of deterring crime using the kit.

21 Claims, 6 Drawing Sheets

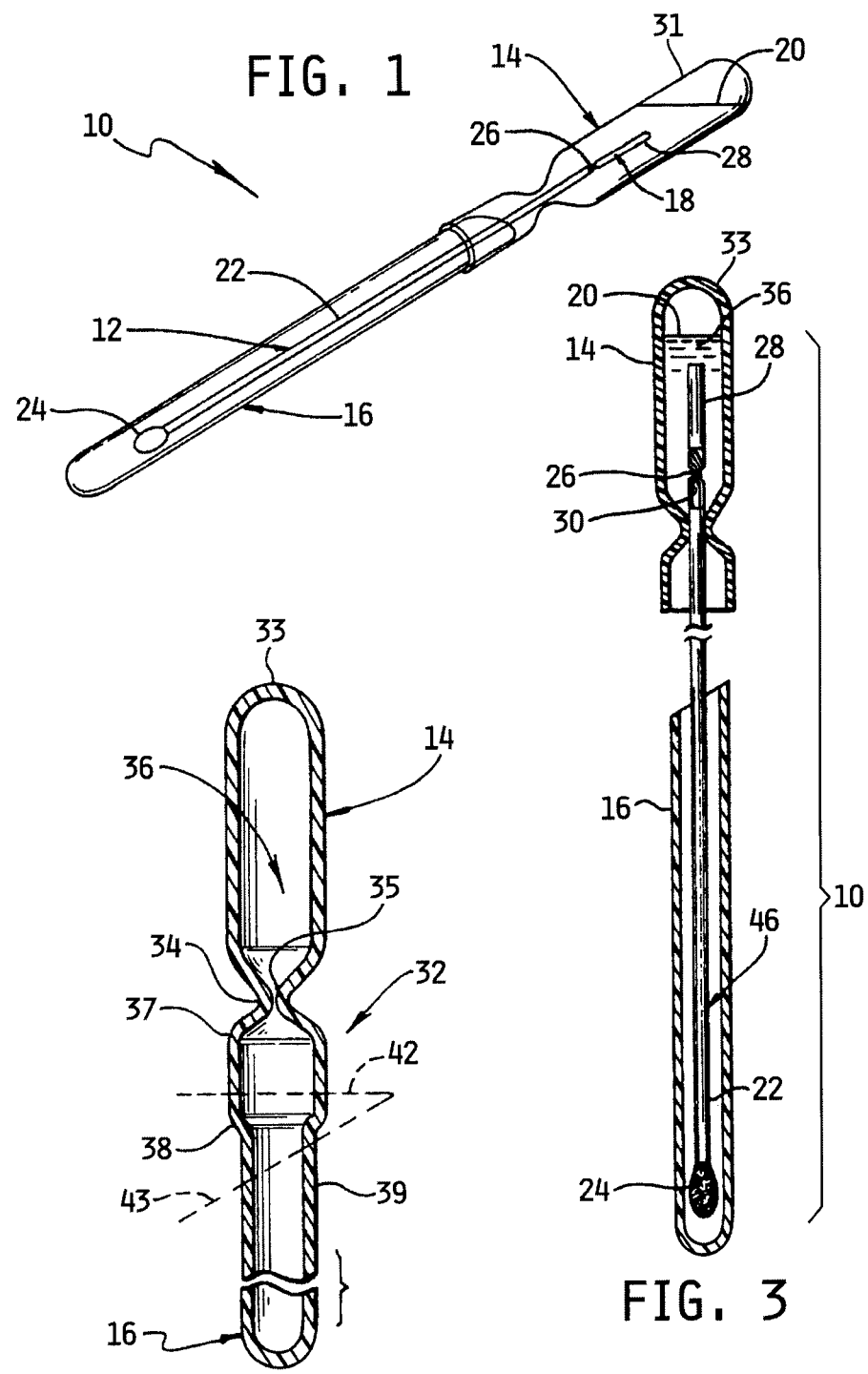

SPECIMEN GATHERING DEVICE AND METHOD OF USE

This application claims the benefit of and priority to U.S. Provisional Patent Application No. 60/959,703, filed 16 Jul. 2007, the disclosure of which is now incorporated herein by reference.

FIELD OF THE INVENTION

The present invention relates generally to a specimen gathering device, and more specifically to a specimen gathering device that can collect, preserve and transport biological specimens.

BACKGROUND OF THE INVENTION

Numerous tools may be used to obtain criminal evidence, as well as to investigate crimes. Currently, DNA is the type of evidence that is gathered and secured only when a specially trained crime scene technician is on the scene. However, there are times when crime scene technicians cannot be on the scene, as they may be at more "urgent" crime scenes, thus leaving the officer or investigator to his or her own devices. This can allow for important evidence to be either missed or destroyed accidentally by officers on the scene.

The previous gathering of DNA has shown that an accidental microbial mixture of DNA (a sample containing a mixture of DNA from every person that touched an item of interest such as for example a gun, including law enforcement and crime lab personnel's DNA) often occurs, causing any sample to be inconclusive upon analysis. This problem has been seen in crime laboratories attempting to analyze swabs from weapons, as well as other swabs containing DNA that become contaminated from improper handling. This DNA is generally referred to as "contact DNA", as it is DNA recovered from an item that is simply touched by a person. Historically, DNA has only been gathered from wet surfaces, such as saliva and blood, and the collection device was then dried to preserve the DNA.

Weapons are often used in crimes. For example, firearms are used throughout the world as the weapon of choice for facilitating crimes. When a firearm is recovered, the current method of attempting to identify who used or handled the firearm is by fingerprinting. This, however, has not yielded very positive results (only 3-5% of firearms that are finger printed yield a result, as firearms are not manufactured to yield fingerprints). Law enforcement personnel also have attempted to use Gun Swab Residue tests, taken from the hand of a person suspected of firing a gun, as gun powder will sometimes leave a residue on the skin of a person who fired it. This test has also been seen as unreliable. (See *Anoka, Minnesota Judge Rejects Gunshot Residue Evidence, Pioneer Press*, May 13, 2006, David Orrick). Fingerprinting as well has been challenged as unreliable, under the Daubert standard expert test. (See *United States v Harvard*, 260 F.3d 537 (7th Cir. 2001)). This was the first of many challenges concerning the actual "science" of both gathering and analyzing fingerprints. Although courts recently have upheld fingerprinting and its analysis techniques, there are current cases pending challenging both the fingerprints and the techniques used in obtaining an identification from fingerprints. For example, see *Grandfathering evidence: fingerprint admissibility rulings from Jennings to Llera Plaza and back again*, American Criminal Law Review, June 2004, Cole, Simon A. It is not clear if these current challenges will be upheld, however, it is indicative of how the "science" of fingerprinting is being disputed by defense attorneys and others. As police and other law enforcement personnel investigate crimes, DNA often is the best evidence that can be gathered to assist in identifying a suspect.

The problem historically is that although DNA can be gathered from firearms, or from other target items or surfaces, doing so at the actual scene is often inconvenient and difficult for law enforcement officers to complete. Moreover, currently officers have to obtain distilled water, which can be cumbersome and inconvenient to carry with them, and place it on a swab to attempt to gather any DNA. Also, conventional DNA gathering techniques require the gathered specimen to be dried prior to analysis. Similarly, conventional DNA gathering techniques do not protect the gathered specimen from contamination by for example mold and/or bacteria.

What is needed is a device and process that will allow users to gather a biological specimen, such as for example and without limitation a DNA specimen, without concern that the specimen will degrade if not dried immediately. It is also desirable that the gathered specimen will be preserved or protected from contamination from for example and without limitation touch/contact DNA, bacteria and/or mold. It is also desirable that the specimen gathering device and method be capable of gathering a specimen from any surface, wet or dry, where a biologic can be deposited. The process for gathering the specimen(s) should be relatively easy to use and teach.

Currently there are patents that assist in this process. For example, see generally, the following related U.S. patents, the disclosures of which are now expressly incorporated herein by reference: U.S. Pat. No. 4,707,450 dated November 1987 to Nason; U.S. Pat. No. 4,978,504 dated December 1990 to Nason; U.S. Pat. No. 5,266,266 dated November 1993 to Nason; and U.S. Pat. No. 6,248,294 dated Jun. 19, 2001 to Nason. However, the specimen gathering kit and the manner in which the specimen gathering kit is used are both unique and novel.

SUMMARY OF THE INVENTION

The present invention may comprise one or more of the following features and combinations thereof described herein below and in the claims appended hereto.

The present invention is intended and designed to gather biological specimens, such as for example and without limitation DNA, from target areas or items, including for example weapons, narcotics, automobiles, containers, structures, people or animals, and the like on the scene. The illustrative embodiments eliminate the wait for the crime lab personnel to arrive on the scene to perform the gathering or collection action, or the delay in taking the item to the lab for personnel to perform the collection or gathering at the lab thereby also avoiding the potential loss of DNA which normally occurs when the target item is sent through the chain of evidence. For example, prior to the present invention, DNA became both compromised and lost due: to the initial and subsequent handling by multiple people with the chance that each person may deposit additional touch or contact DNA on the target, to the need to transport the weapon to the lab prior to taking a specimen, and to the length of time before the weapon is actually swabbed by crime lab personnel. The illustrative embodiments disclosed herein may eliminate the chances of additional DNA being on the gun, as the illustrative embodiments call for a user, such as for example a law enforcement officer, to swab the gun at the scene, virtually protecting any DNA immediately after the gun has been recovered and without the need to first dry the specimen prior to transport.

This invention relates generally to an easy-to-use, self-contained kit or device for the collection or gathering of biological specimen(s), for example and without limitation DNA, from desired targets, for example and without limitation from a weapon such as a firearm and from a crime scene in general, and be readily used by law enforcement and crime laboratory personnel. The device is self-contained and uses a solution that both enhances DNA and destroys bacteria that may potentially degrade DNA. The solution contains a preservative. The preservative may be a biocide. The biocide may comprise an antimicrobial. Illustratively, the solution and the swab are self-contained in a single device, allowing for easy transport and use. The gathering of DNA from targets such as for example a weapon has been attempted with some success, however, this has been done in the crime laboratory, and rarely on the scene, which allowed the weapon to be handled by numerous people, including the suspect. This lack of process and the lack of a DNA gathering tool can be solved with the device. Law enforcement can be trained in the appropriate process to gather DNA at the scene, using the device. The illustrative embodiments can be used to collect biological specimen(s) from any target or item of interest including for example and without limitation firearms, in a manner that will enhance and preserve or protect the DNA gathered, as well as keep the DNA from degrading.

Illustrative specimen gathering device(s) and kit(s) are disclosed. The illustrative specimen gathering kit generally comprises a specimen gathering unit or device. The specimen gathering device may be transported in one or more containers. The container(s) may comprise one or more bags. The illustrative specimen gathering unit or device is provided for use in collecting a biological specimen, such as for example and without limitation a DNA sample or other biologic or biological molecule including tissue, cells, and/or body fluid. The illustrative specimen gathering unit or device also preserves or protects, from contamination and the like, the gathered specimen during transport and/or storage. Illustratively, the gathered, protected and preserved specimen may be subjected to a selective test(s) subsequent to being gathered. Such test(s) may be done without any need to freeze or dry the specimen. The specimen gathering unit illustratively is self-contained and comprises the combination of a swab member and a solution enclosed within interfitting housing components, namely, a housing base and a housing cap. The swab member illustratively may include a moveable valve or nib. The moveable nib generally seals or contains the solution within the housing base until it is desired to charge the device for use by releasing the solution to allow it to come into fluid communication with the swab tip.

The present device decreases the prevalence of contact DNA from other than the suspect or victim while gathering, enhancing and preserving, until it is ready to be analyzed, the contact DNA of the suspect or victim. The present device obtains DNA from dry surfaces, gathering DNA as the swab moistens the target, for example a gun, with the solution.

Thus, the present invention is directed toward not only the collection, but the transportation of the DNA specimen or evidence collected. The present device allows for users to carry a portable swab, including a self-contained solution that enhances DNA and neutralizes enzymes that can potentially grow mold and/or bacteria. This allows for evidentiary DNA to be collected or gathered at the scene, rather than waiting for crime lab personnel to perform the gathering, either at the scene or subsequently in the lab. Thus, any DNA that would have been contaminated at the scene and/or lost in the transportation process is now already gathered and protected within the device.

Although most similar collection devices have advocated the drying of the DNA evidence once it is gathered on a wet swab, the current device need not be and will not actually dry for some time. Moreover, the self-contained solution will protect the gathered DNA, rather than degrade the DNA. Therefore, should the device be used properly, and the specimen properly collected is subsequently tested for DNA, DNA will still be present both when the swab is wet and upon the drying of the swab. Thus, the timing of the drying or testing of the illustrative swab is not as urgent as previously required. Rather, the preservative the specimen gathering solution can dry on its own, within the plastic tube the swab is held.

The illustrative specimen gathering device(s) generally comprise a transport housing, swab member and a solution. The solution comprises a preservative that enhances biologic samples such as for example DNA and is also an anti-bacterium that kills bacteria before it forms in the housing that contains the swab member and any gathered specimen. The illustrative kits comprise a container in which the specimen gathering device(s) are inserted. The swab member has opposing ends. One end comprises a swab and the opposite end comprises a swab nib. The housing comprises a base and an interfitting cap. The housing base defines a solution chamber having a closed end and an opposite open end. The solution is received within the solution chamber. The swab member is lodged within the base with the swab nib extending into the solution chamber and the swab tip protruding from the open end of the solution chamber. The swab member seals the open end of the solution chamber to contain the solution therein.

A method of use is also disclosed. The method generally comprises the steps of: providing a specimen gathering kit including a re-sealable container having therein a self-contained specimen gathering device including a preservative solution; opening the seal on the re-sealable container; removing the specimen gathering device from the container; charging the specimen gathering device with the preservative solution; gathering a specimen; returning the specimen gathering device to the container; and re-sealing the container.

The method may further include providing a holistic training, educating, analyzing, promoting, and deterrence process.

In one illustrative use, a user illustratively will locate or a target of interest, such as for example a weapon. The user will then proceed to secure the area, without handling the target. Once the area is secure, the user illustratively will place on protective gloves, (such as latex gloves), will then remove the first swab from a container such as a plastic bag, which is closed to ensure no contamination exists upon the initial swabbing of the target. Once the first swab is removed from the bag, the user will move the nib to break the nib or valve at the top of the swab (by simply using his or her thumb to push the swab either to the left or the right, which cracks the protective plastic containing the solution), then squeeze the bulb to ensure all the solution is in fluid communication to be absorbed by the swab itself. Once the swab becomes absorbed with the solution, or charged, the swab is removed from the tube, allowing for the user to first swab the slide or barrel of the gun, depending on the type of weapon recovered. The swab is then covered again by the plastic tube and is placed back in the container or bag that contained it originally. The weapon is then unloaded and secured, and the previous steps are followed, and the trigger and handle are then swabbed, and the swab is again placed back in the bag. The bag is then sealed with an adhesive tape or other sealing means that is on the bag, and the user signs the bag to ensure the bag is only opened after it has gone through the chain of evidence and to the designated laboratory for testing. When the above described process is completed properly, laboratories are able to extract the DNA from the swab much like is currently performed with a buccal swab, as the solution does not inhibit the reagents typically used by criminal laboratories to enhance and analyze DNA.

These and other objects of the present invention will become more apparent from the following description of the illustrative embodiment(s).

BRIEF DESCRIPTION OF THE DRAWINGS

FIG. 1 is an exploded perspective view of an illustrative specimen gathering device;

FIG. 2 is an enlarged fragmented vertical sectional view of an illustrative housing for use with the illustrative specimen gathering device of FIG. 1;

FIG. 3 is a fragmented and partially exploded vertical sectional view illustrating further aspects of the illustrative specimen gathering device of FIG. 1;

DESCRIPTION OF THE ILLUSTRATIVE EMBODIMENTS

Figure 4:
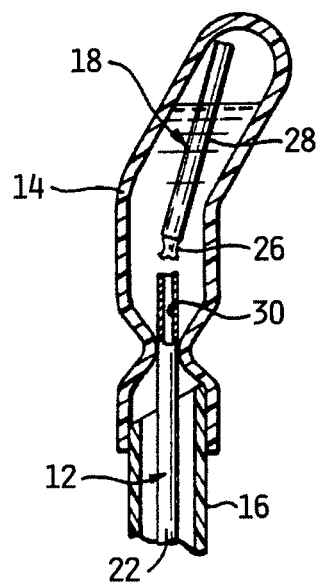
FIG. 4 is an enlarged fragmented vertical sectional view depicting deformation of a housing base to sever a break-off nib from a swab member of the illustrative specimen gathering device of FIG. 1.

For the purposes of promoting an understanding of the principles of the invention, reference will now be made to a number of illustrative embodiments illustrated in the drawings and specific language will be used to describe the same.

The following definitions and descriptions are generally applicable to all of the illustrative embodiments:

The terms "specimen," "sample" and "evidence" are used to specify a specimen, sample or evidence, of for example a biologic, collected or gathered by the illustrative specimen gathering device or unit 10. These terms are used almost interchangeably, as the present illustrative device 10 will collect a specimen or sample of biological material, such as for example DNA, from an item of interest or target, for example and without limitation a weapon such as for example a gun or firearm, which specimen will, during the process, illustratively become DNA evidence. Unlike samples previously gathered using other devices, the specimen(s) or sample (s) collected with the present device 10 may be taken from dry surfaces. Illustratively, biologic samples containing DNA include saliva, blood, human or animal tissue, hair, urine or fecal matter, food products or other microbial items.

As used herein, the term "swab" or "swab member" 12 refers to the elongated member that generally comprises an elongated "shank" or "shaft" 22 and a "swab tip," 24 which refers to the gathering or collection end or tip 24 of the illustrative gathering or collection device 10, and which illustratively is made for example and without limitation of Aquazone Foam, which is made and manufactured to create an advantageous material to soak the solution into the tip of the device, and maintain any DNA or other specimen gathered into the swab. The swab 24 may also be fashioned of rayon, cotton, polyester, and other natural, synthetic and/or composite materials as further described herein. The elongated "shank" or "shaft" 22 of the swab member 12 illustratively may be plastic or other suitable material. In addition, the shaft 22 may be solid or hollow as will be described.

The "transportation device", "tube" or "housing components" describe the plastic tube or housing 14, 16 that releasably interfit with one another to house or encase and protect the swab 12. The swab 12 and the housing components illustratively initially are sterile until the valve or nib 18, 40, 52, 74 is moved, displaced or broken, allowing the solution 20 to flow out of the housing base 14 and into the housing cap 16 and/or until the base 14 and cap 16 are first separated from one another. As will be explained, once the base and cap are separated from each other and the swab tip 24 has been used to gather or collect a specimen, the housing base 14 and cap 16 are rejoined together to protect the swab 12 during storage and/or transportation to for example the crime laboratory. Thus, the housing components 14, 16 double as the device that keeps the swab 12 protected and sterile prior to use, and the device that subsequently preserves and protects the gathered specimen during transportation and storage.

The "bulb" 31 referred to herein is the deformable upper portion of the housing base 14, illustratively it may also be made of durable plastic and generally defines a solution chamber 36 that contains the solution 20, which solution 20 illustratively is used to gather and preserve any gathered specimen.

The "valve" or "nib" 18, 40, 52, 74 refers to an illustratively plastic piece within the aforementioned bulb 31 or housing base 14. The valve or nib illustratively acts as a stop gap in the bulb, ensuring the solution 20 is sealed, contained or maintained within the solution chamber 36 prior to sufficient movement or displacement of the nib. In one illustrative embodiment, once the valve is broken, the tip of the valve remains loose inside the bulb, and the solution is allowed to flow out of the solution chamber 36 and into the housing cap 16, and perhaps fluid communications with the swab tip 24.

The "solution" 20 refers to the liquid initially contained in the solution chamber 36. The solution 20 illustratively is a buffer solution. Illustratively the solution includes a preservative and is used to gather, enhance and preserve biological specimens such as for example and without limitation DNA. As noted, the illustrative solution 20 will both enhance the collection of biologic specimen(s), such as for example DNA, and preserve the specimen for example by, among other things, preventing the formation of bacteria, mold or fungus even though the specimen remains wet. To this end, the solution comprises a preservative, which illustratively comprises a biocide, and more illustratively comprises an anti-microbial. Accordingly, the specimen collected with the solution need not be dried prior transport or testing. In addition, to being able to gather or collect a specimen from any wet or dry surface containing DNA, including from blood, the illustrative solution 20 can even gather "contact" or "touch" specimen(s) of for example DNA and the like. Such "contact" or "touch" DNA specimens may comprise from 150 to 160 cells or about one (1) nanogram. The illustrative specimen gathering device generally is able to gather at least contact DNA, which is more than "low copy" specimens of DNA, which equates to about 20 to 100 cells, or less than one (1) nanogram. Illustratively, there is approximately enough solution to ensure the swab tip 24 becomes damp when the specimen gathering device is charged by releasing the solution 20 and allowing it to come into fluid communications with the swab tip. The solution 20 illustratively and generally comprises in suitable amounts or concentrations: Ethylenediaminetetraacetic acid (EDTA), Sodium Chloride, Sodium phosphate, dibasic, potassium phosphate, monobasic, potassium chloride, glycerol, and a preservative such as for example a biocide. Illustrative concentrations comprise for example and without limitation Ethylenediaminetetraacetic acid (EDTA)—0.5 mM, Sodium Chloride—about 137.0 mM, Sodium phosphate, dibasic—about 9.8 mM, potassium phosphate, monobasic—about 2.1 mM, potassium chloride—about 2.7 mM, glycerol—about 5%, and a preservative ranging between about 0.001% to about 1.0%. One illustrative solution 20 generally comprises: about 140 to 150 mg of Ethylenediaminetetraacetic Acid (EDTA), about 7.0 to 9.0 g of Sodium Chloride (NaCl), about 2.0 to 3.0 grams of Sodium phosphate, dibasic ($Na_2HPO_4$), about 280.0 to 290.0 mg of Potassium phosphate, Monobasic ($K_2HPO_4$), about 195.0 to 205.0 mg of Potassium chloride (KCl), about 60.0 to 65.0 g of Glycerol ($C_3H_8O_3$) and about 150 to 250 µl of a preservative, biocide or anti-microbial. In one illustrative embodiment, the solution illustratively comprises: about 146.1 mg of Ethylenediaminetetraacetic Acid (EDTA), about 8.0 g of Sodium Chloride (NaCl), about 2.91 grams of Sodium phosphate, dibasic ($Na_2HPO_4$), about 285.79 mg of Potassium phosphate, Monobasic ($K_2HPO_4$), about 201.29 mg of Potassium chloride (KCl), about 63.05 g of Glycerol ($C_3H_8O_3$), and about 200 µL of Kathon preservative, with the foregoing diluted to 1.0 L with ultrapure water as known to those skilled in the art. Other suitable buffer solutions fall within the scope of the invention. The biocide illustratively comprises an anti-microbial. Illustratively, the biocide comprises a product sold under the trademark Kathon®, for example and without limitation Kathon® CG/ICP II. Another suitable biocide comprises a product sold under the trademark ProClin™. Other suitable preservatives fall within the scope of the invention so long as they provide an antimicrobial ability to eradicate and control, among other things, bacteria, yeast, and fungi growth and activity over an extended period of time, while being compatible with certain enzymes, and while not interfering with the specimen gathering device's ability to take biological specimens including for example DNA samples. Such suitable preservatives illustratively should also have excellent stability, be effective over a broad pH range, for example and without limitation pH 2-12 or so, and not be overly toxic. The solution could also comprise distilled water and/or the specimen gathering device could be used with a solution of distilled water alone, whether contained within the device 10 or not.

It will be appreciated that the solution could also comprise one or more components that allow the solution to change colors upon contact with a selected material such as for example the swab 12, and/or a certain biologic. For example, the swab could be impregnated with a certain indicator that changes colors when coming in contact with the solution 20, or vice versa. So, too, an indicator could be used that changes color when coming into contact with any other selected item or material, such as for example blood. Any suitable indicator could be used including for example and without limitation: phenolphthalein, thymolphthalein, gentian violet, leucomalachite green, thymol blue, methyl yellow, bromophenol blue, congo red, methyl orange, bromocresol green, methyl red, azolitmin, bromocresol purple, promothymol blue, phenol red, neutral red, naphtholphthalein, cresol red, and alizarine yellow R, or other indicator as desired and known to those skilled in the art. So, too, the specimen gathering device 10 could comprise any suitable means of illumination. For example, the specimen gathering device 10, or kit, or any selected component(s) thereof, may comprise luminescence properties caused by any combination of chemical reactions, electrical energy, subatomic motion or stress on a crystal. For example and without limitation the kit or any portion thereof may be luminized or coated with luminescent materials or with radioactive materials, that do not interfere with the viability of the specimen. The following illustratively all fall within the scope of the invention: chemoluminescence, crystalloluminescence, electroluminescence, mechanoluminescence, photluminesence, radioluminescence, sonoluminescence, and thermoluminescence. In addition, the device may be illuminated using known incandescence and/or fluorescence techniques and means. Other means may be used as well including for example a light emitting diode. Fluorophore's may also be used.

The "kit" refers to various illustrative pre-packaged specimen gathering devices. While a kit could illustratively comprise a single specimen gathering device 10; it is desirable that each of the kits will comprise at least one re-sealable or re-closeable container such as for example and without limitation a plastic bag, baggie, or package 11, 13 containing at least one (1) specimen gathering device 10. Illustratively, a kit may comprise two (2), three (3) or more than three (3) specimen gathering devices 10. Further illustratively, the kit may comprise two (2) or more containers or baggies 11, 13. Thus, for example a kit illustratively may initially include a single specimen gathering device 10 disposed within an initially sealed insert container or baggie 11, which together are disposed within an initially sealed and re-sealable evidence container or baggie 13. Similarly, in another embodiment, the kit illustratively will initially include two (2) specimen gathering devices 10 each disposed within an initially sealed insert baggie 11, which together are disposed within a sealed and re-sealable evidence baggie 13. In yet another illustrative embodiment, the kit illustratively will initially include three (3) specimen gathering devices 10 each disposed within a sealed insert container or baggie 11, which together are disposed within a sealed and re-sealable evidence container or baggie 13. Although a single insert container or baggie is used in each of the foregoing illustrative embodiments, it will be appreciated that a separate insert bag 11 could be used for each specimen gathering device in the respective illustrative kit. It will be appreciated that a kit may include means to allow the kit to easily be carried on various pieces of equipment for example and without limitation on a flashlight, in a backpack, in an evidence bag, on a utility belt, and the like. For example, the kit may comprise Velcro, two-sided tape, ties, snaps, clips, clamps and the like configured to secure the kit to equipment. The kit illustratively may further comprise instructions on how to use the kit to collect a specimen. The instructions illustratively may comprise printed inserts received in the container(s), and/or may be printed on the container(s).

The specimen gathering unit or device 10 illustratively gathers biological specimens at the target, such as for example a crime scene, as well as allows the specimen to be transported wet, rather than having to first dry the sample as previously has been done. The device 10 illustratively is made of durable plastic and a resilient swab tip, it illustratively functions as one unit to both gather and transport DNA. The solution 20, which illustratively is a buffer solution and is contained at the top of the swab 12 in the solution chamber 36 generally defined by the bulb 31 of the base 14, will not come into contact or fluid communication with the swab tip 24 until the device 10 is charged as when snap valve or nib 18, 40, 52, 74 is moved, displaced or broken by the user to open or unseal the solution chamber. The snap valve 18, 40, 52, 74 will block or contain the solution in the solution chamber 36 until the valve is moved, displaced or broken as described herein. Once the snap valve is moved, displaced, or broken, the solution may flow out of the chamber 36 due to gravity, and/or the bulb containing the solution 20 may be squeezed to ensure substantially all the solution is out of the bulb.

Once the valve 18, 40, 52, 74 is broken and the solution 20 is emptied from the solution chamber 36 into the plastic casing and onto or into fluid communication with the swab tip 24, the swab 12 is charged or ready for use. Illustratively, the solution 20 of the illustrative specimen gathering device 10 will allow biologic specimens, including for example and without limitation DNA to be gathered and protected within the swab and transportation or transport housing 14, 16 without the development of bacteria, mold or other harmful enzymes that generally degrade biologic specimens such as the exemplary DNA.

Referring to FIG. 1 through FIG. 16 illustrative specimen gathering device(s) and kit(s) are disclosed. As noted, the illustrative specimen gathering kit 10 generally comprises a specimen gathering unit or device 10 and container(s) or packaging comprising one or more bags 11, 13. The illustrative specimen gathering unit or device 10 is provided for use in collecting a biological specimen, such as for example and without limitation a DNA sample or other biologic or biological molecule including tissue, cells, and/or body fluid. The illustrative specimen gathering unit or device 10 also preserves or protects, from contamination and the like, the gathered specimen during transport and/or storage. Illustratively, the gathered, protected and preserved specimen may be subjected to a selective test(s) subsequent to being gathered. Such test may be done without any need to freeze or dry the specimen. The specimen gathering unit 10 illustratively is self-contained and comprises the combination of a swab member 12 and a solution 20 enclosed within releasably interfitting housing components, namely, housing base 14 and housing cap 16. The swab member 12 illustratively may include a valve or nib 18, 40, 52, 74 which may or may not be a break-off nib, to permit delivery of the solution 20 to contact a swab tip 24.

Now that general aspects of all of the illustrative embodiments have been described, a more specific description of each illustrative embodiment will be provided. As shown in detail in FIGS. 1-5, with respect to one illustrative form of the invention, the illustrative specimen gathering unit 10 generally comprises an elongated, relatively thin implement having an overall size and shape for easy manual handling during use. The illustrative swab member 12 is shown with the elongated shank or shaft 22 having a front end supporting the swab tip 24 of for example and without limitation Aquazone Foam, rayon, cotton, Dacron, polyester, or other absorbent fibrous material which may be wrapped, woven, non-woven or conductive, and which may be wound or otherwise suitably attached to the shaft 22. It will be understood, however, that other types of swab tips such as a brush or the like may be used. The swab shaft 22 illustratively is formed from a molded plastic or any other suitable material to have a relatively stiff but somewhat flexible construction corresponding generally with conventional swabs.

An opposite or rear end of the swab shaft 22 comprises an illustratively break-off nib 18. Illustratively, the rear end of the swab shaft 22 is joined at a reduced diameter score 26 with a solid rod segment 28 formed as a continuation of the swab shaft. A central bore 30 (FIGS. 3-5) defined by the hollow shaft 22 terminates generally at the score 26, whereby the solid rod segment 28 effectively closes the rear end of the swab shaft against fluid inflow. The swab 12 illustratively may range in size from about an inch or less to about a foot or more depending on the size of the target from which specimen (s) will be taken. The swab tip 24 illustratively can have a height and width ranging from less than an inch to an inch or greater, also depending on the target size and/or the nature of the surface to be swabbed and other considerations as desired.

The swab member 12 illustratively is normally positioned within the housing components 14 and 16, with the resultant specimen gathering unit 10 being provided as a preassembled and generally sterile unit 10. The housing components constitute a housing base 14 formed with an illustratively and generally cylindrical shape to include an upper deformable squeeze bulb 31 and having one closed end 33 and an opposite open end. The housing base 14 is adapted for a sliding, sealed interfit with the elongated and generally cylindrical housing cap 16. Both of these housing components 14 and 16 illustratively are conveniently and desirably constructed, for example as by blow molding, as lightweight and economical plastic elements. Other suitable materials and methods of manufacture suitable for those materials may be used. It will be appreciated that other forms of connection, including for example and without limitation a screw fit or a snap fit, fall within the scope of the invention.

The housing components 14 and 16 illustratively may be manufactured as a unitary blow molded element 32, as viewed in FIG. 2. That is, the unitary element 32 defines the housing base 14 having a closed end 33. From the closed end 33, the housing base extends with a generally cylindrical geometry to a seal collar 34 of reduced diametric size defining a narrow aperture 35 opening into a solution chamber 36. From the seal collar 34, the housing base expands to a larger diametric size to define a female housing fitting 37. This fitting 37 is joined integrally to the housing cap 16 by means of a transition shoulder segment 38 which reduces the diametric size of the blow molded element 32 to define an upper end 39 for the housing cap 16. The cap upper end 39 has a diametric size for sealed, slide-fit reception as a male fitting into the female housing fitting 37. The blow molded element 32 is separated into the housing base and cap 14 and 16 by appropriately cutting in the region of the shoulder segment 38. A first cut 42 near a lower end of the fitting 37 separates the base and cap into two discrete components, and a second cut 43 at a position slightly below the shoulder segment 38 permits sealed slide-fit reception of the cap upper end 39 into the fitting 37. The second cut 43 is conveniently formed at an angle, as shown in FIG. 2, to accommodate facilitated slide-fit engagement of the housing base 14 and housing cap 16. Illustratively, the housing base 14 is adapted to receive the liquid solution 20 into the solution chamber 36, which is generally defined by the squeeze bulb 31. In this regard, the solution 20 illustratively is placed into the chamber 36 via the aperture 35. After the solution chamber is appropriately filled, the rear end of the swab shaft 22 is slidably pressed into the aperture 35, in sealing engagement with the seal collar 34. The swab shaft is pressed into and through the aperture 35 to place the score 26 at least a short distance into the solution chamber 36, as viewed in FIGS. 1 and 3. The housing cap 16 is then fitted over the protruding swab shaft 22 and tip 24, in slide-fit sealed relation with the fitting 37 on the housing base 14.

When use of the specimen gathering device or unit 10 is desired, for purposes of collecting a biological specimen or the like, the housing cap 16 and the housing base 14 illustratively are slidably separated from one another to expose the swab shaft 22 and the associated swab tip 24, which protrude from the housing base 14. In this configuration, the housing base 14 provides a convenient handle for manual manipulation of the swab member 12 to collect a selected specimen on the absorbent tip 24. After the specimen has been collected, the housing cap 16 and the housing base 14 are slidably re-joined together to enclose the swab tip 24 with the collected specimen thereon. In this configuration, the interfitted housing base 14 and cap 16 cooperatively define a specimen chamber 46 with the swab tip 24 disposed therein and protected thereby during transport and/or storage.

Figure 5:
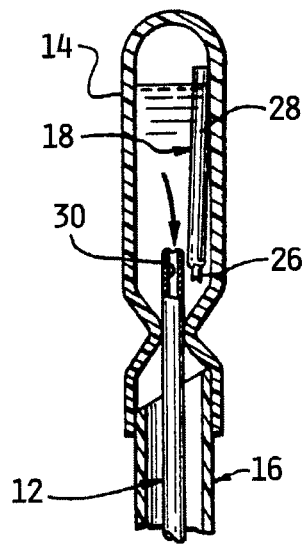
FIG. 5 is an enlarged fragmented vertical sectional view similar to FIG. 4, and illustrating solution flow through a hollow shaft of the swab member.

As shown in FIGS. 4 and 5, the resiliently deformable plastic material of the squeeze bulb 31 illustratively permits manual movement, displacement, or bending of the housing base 14 sufficiently to move, displace or break off the nib 18 at the rear end of the swab shaft 22. That is, such deformation of the squeeze bulb 31 of the housing base 14 is effective to bend the rod segment 28 relative to the shaft 22 to break the rod segment 28 at the narrow score 26. Such break-off action opens the rear end of the swab shaft 22 for solution inflow from the solution chamber 36. A slight application of manual squeeze pressure to the squeeze bulb 31 is effective to deliver a substantial portion of the solution out through the hollow shaft 22 for purposes of contacting or communicating with the swab tip 24. In this regard, deformation of the housing base 14 sufficient to sever the nib 18 (FIG. 4) will normally deform and compress the solution chamber 36 to provide substantially immediate solution delivery when the nib breaks thereby charging the device 10 for specimen gathering. When the housing cap 16 and the housing base 14 are joined together before solution dispensing, a pool may be formed within the specimen chamber 46.

Figure 6:
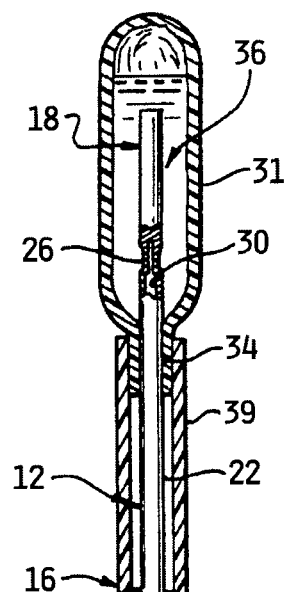
FIG. 6 is an enlarged fragmented vertical sectional view similar to FIGS. 4 and 5 and depicting one alternative embodiment of the invention.

FIG. 6 illustrates an alternative embodiment, wherein components identical to those shown and described in FIGS. 1-5 are referred to by common reference numerals. In the illustrative embodiment of FIG. 6 the overall construction and operation of a modified test unit are the same as the embodiment of FIGS. 1-5, except that the bell-shaped fitting 37 is omitted from the housing base 14. Instead, the upper end 39 of the housing cap 16 is shaped for sealed and slide-fit reception over the narrower diameter seal collar 34. Once again, the break-off nib 18 on the rear end of the swab shaft 22 projects into the solution chamber 36 generally defined by the deformable squeeze bulb 31, and the base 14 is sufficiently deformable to permit the nib 18 to be moved or severed from the swab shaft 22 when solution dispensing or charging for use is desired.

Figure 7:
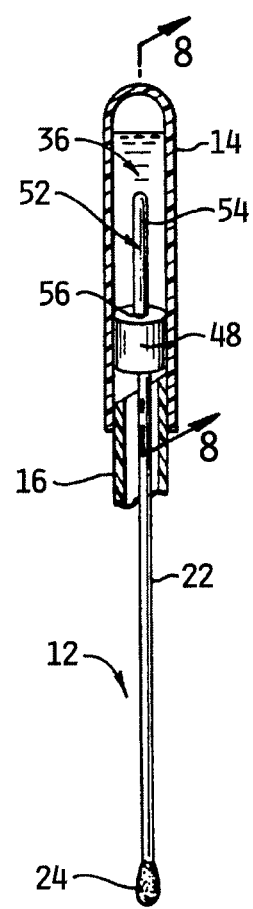
FIG. 7 is a fragmented perspective view depicting another illustrative specimen gathering device.
Figure 8:
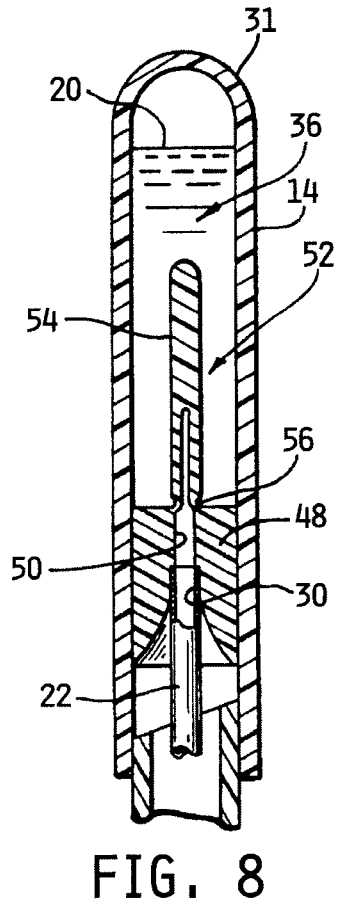
FIG. 8 is an enlarged fragmented vertical sectional view taken generally on the line 8-8 of FIG. 7.
Figure 9:
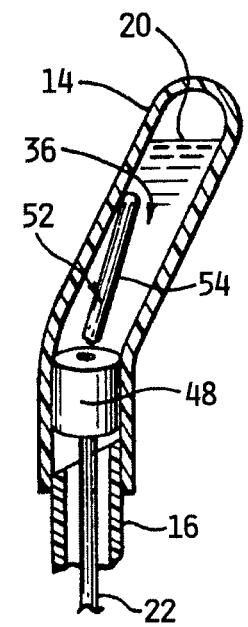
FIG. 9 is a fragmented perspective view depicting deformation of a housing base to sever a break-off nib, corresponding with the embodiment of FIGS. 7 and 8.

FIGS. 7-9 illustrate another alternative illustrative embodiment, wherein components corresponding in structure or function with those described in FIGS. 1-6 are again identified by common reference numerals. In this illustrative embodiment (FIGS. 7-9), a modified housing base 14 includes a deformable squeeze bulb 31 and has a generally cylindrical, open-ended construction adapted for slide-fit sealed reception of a seal fitting 48 into the open end thereof. The seal fitting 48 can be formed as an injection molded plastic component or the like and normally closes a solution chamber 36 in the housing base 14 subsequent to filling with a selected solution 20. The seal fitting includes a central dispense aperture or passage 50 (FIG. 8) having an outboard end which is outwardly flared for easy and self-guided press-fit reception of the open upper end of a hollow swab shaft 22. The central passage 50 in the seal fitting 48 is normally closed by a moveable break-off nib 52 in the form of an extended solid rod segment 54 connected to the seal fitting 48 at an inboard end of the passage 50 via a reduced diameter score 56. A housing cap 16 may be provided for slide-fit engagement with the housing base 14 to enclose and protect the swab 12.

The illustrative embodiment of FIGS. 7-9 is utilized in the same manner as described previously with respect to FIGS. 1-6. That is, the housing base 14 can be deformed sufficiently to move or break off the rod segment 54 (FIG. 9), and thereby permit solution delivery through the seal fitting 48 and the swab shaft 22 to charge the swab tip 24. The housing base 14 and associated housing cap 16 are adapted for slidable disassembly and reassembly subsequent to collection of a specimen on a swab tip 24 to enclose the specimen and swab tip 24 within a specimen chamber 46.

Figure 10:
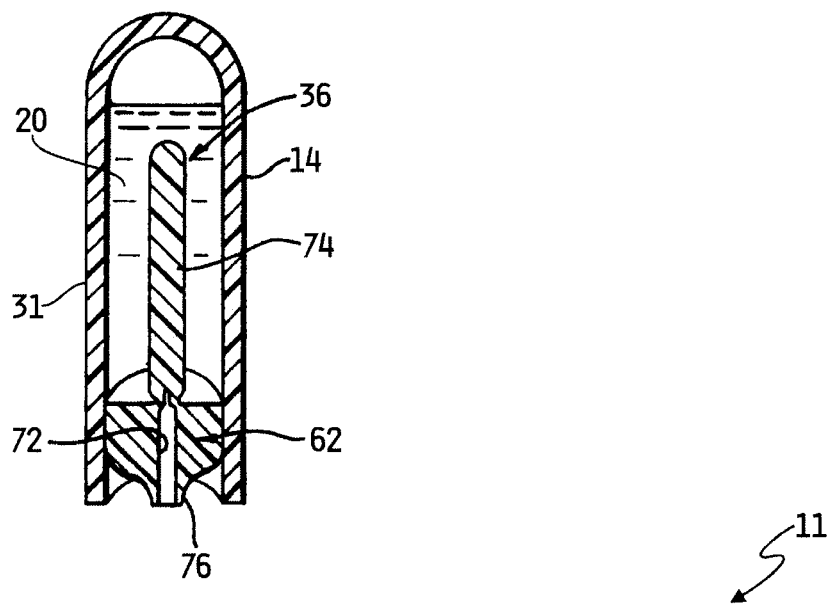
FIG. 10 is a fragmented perspective view of another illustrative specimen gathering device.

Another alternative illustrative embodiment of the specimen gathering device 10 is shown in FIG. 10, wherein a dispense member 62 is installed into the open end of the housing base 14. In this illustrative embodiment, the dispense member 62 includes a central flow aperture 72 which is normally closed by the moveable break-off nib 74. The nib 74 illustratively comprises a solid rod segment projecting into a solution chamber 36 which contains a selected solution 20. The dispense member 62 provides a unitary component for normally sealing the housing cap 14 against solution outflow, yet permitting controlled solution dispensing upon moving or severing the nib 74. More particularly, the base 14 can be deformed quickly and easily as described previously with respect to FIGS. 1-9 to bend and break the nib 74 to open the passage 72 to solution flow. An outboard or nose end of the dispense member 62 conveniently defines a dropper tip 76 to form the dispensed liquid into discrete drops in response to controlled application of manual pressure to the squeeze bulb 31.

In another illustrative embodiment (FIGS. 14-16), the housing base 14 illustratively comprises an outer shell or case of blown or molded plastic to include an upper deformable squeeze bulb 31 joined integrally by a narrowed neck 52 to a lower mounting sleeve 54. The squeeze bulb 31 is sufficiently transparent to permit viewing of an internal closure member, valve or nib 40 illustratively of injection molded plastic or the like fitted therein, with a cylindrical liner 58 pressed into the lower mounting sleeve 54. This liner 58 has an upper end which transitions through the neck 52 and is joined integrally by a thin rupturable or frangible membrane ring 49 to the moveable break-off nib 40 projecting upwardly into the interior of the squeeze bulb 31. A central stem pin 41 is provided as an extension of the moveable nib 40 and projects downwardly from the nib 40 within the liner 58 to engage and sealingly close an outlet port 44 formed in a seal fitting or seal plug 48 pressed into the liner 58.

Figure 14:
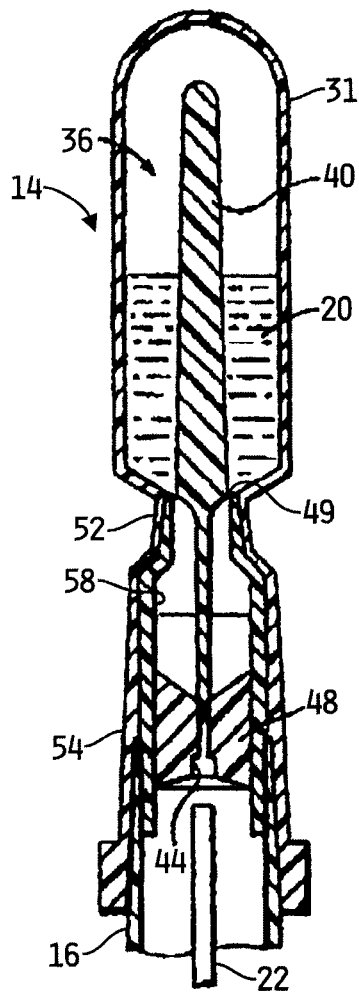
FIG. 14 is an enlarged fragmented vertical sectional view depicting another illustrative specimen gathering device.
Figure 15:
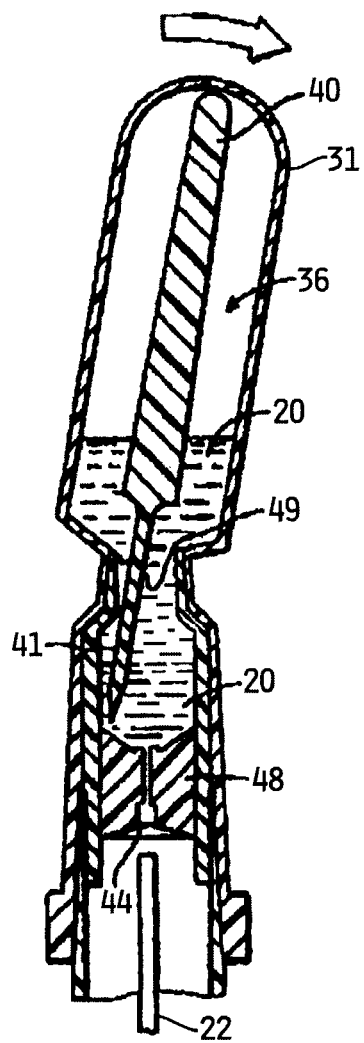
FIG. 15 is an enlarged fragmented vertical sectional view depicting deformation of a housing base to break a nib of the illustrative specimen gathering device of FIG. 14; and similar to FIG. 4, and illustrating.
Figure 16:
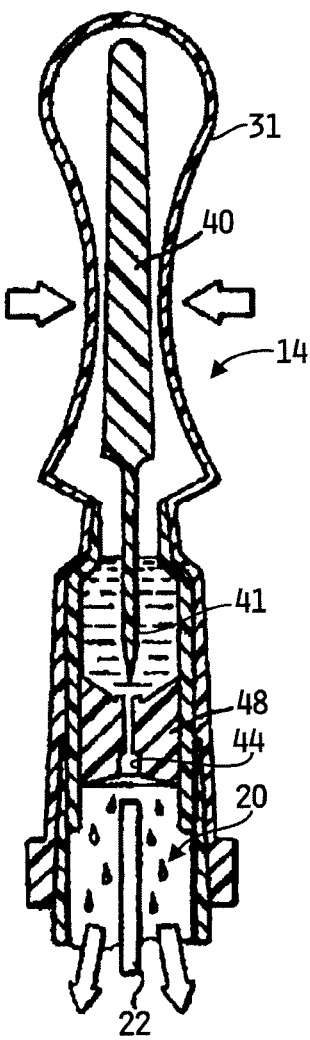
FIG. 16 is an enlarged fragmented vertical sectional view depicting solution out of the base of the device of FIGS. 15 and 16.

The housing base 14 illustratively is assembled in a manner to receive at least one solution 20, shown in liquid form in FIGS. 14-16, in solution chamber 36, which is generally defined by the interior volume of the squeeze bulb 31. Illustratively, a press-fit installation of the nib 40 into the outer case cooperates with the upper end of the liner 58, the neck 52, and the membrane 49 to contain or seal the solution 20 in the solution chamber 36. The nib or valve 40 also has a stem pin 41 that seals or closes the outlet port 44.

The housing base 14 illustratively may be manipulated as by moving, bending or deforming the squeeze bulb 31 through an angular stroke sufficient to cause movement or bend over displacement of the nib 40 to rupture the membrane ring 49, as viewed in FIG. 15. This action breaks the seal between the neck 42 and the membrane 49, thus allowing the solution 20 to flow out of solution chamber 36. Further bendover displacement of the squeeze bulb 31 will retract the stem pin 41 from the outlet port 44 (FIG. 15), whereupon the squeeze bulb 31 can be manually squeezed (FIG. 16) to express the solution 20 through the outlet port 44 into the specimen chamber 46. With the specimen gathering unit or device 10 held in an essentially upright orientation, the solution 20 will drain via gravity to the lower end of the specimen chamber 46 to flood or come into fluid communication with the swab tip 24 to charge the device 10 for use. It will be appreciated that the housing base 14 could be configured such that the solution chamber 36 is sealed only at the neck 52, or only at the seal plug or fitting 48.

It further will be appreciated that other housing bases with alternate means of sealing and unsealing the solution chamber from the specimen chamber fall within the scope of the invention. So, too, any of the illustrative specimen gathering devices 10 may be manufactured from alternate materials using manufacturing methods compatible with such materials.

Figure 11:
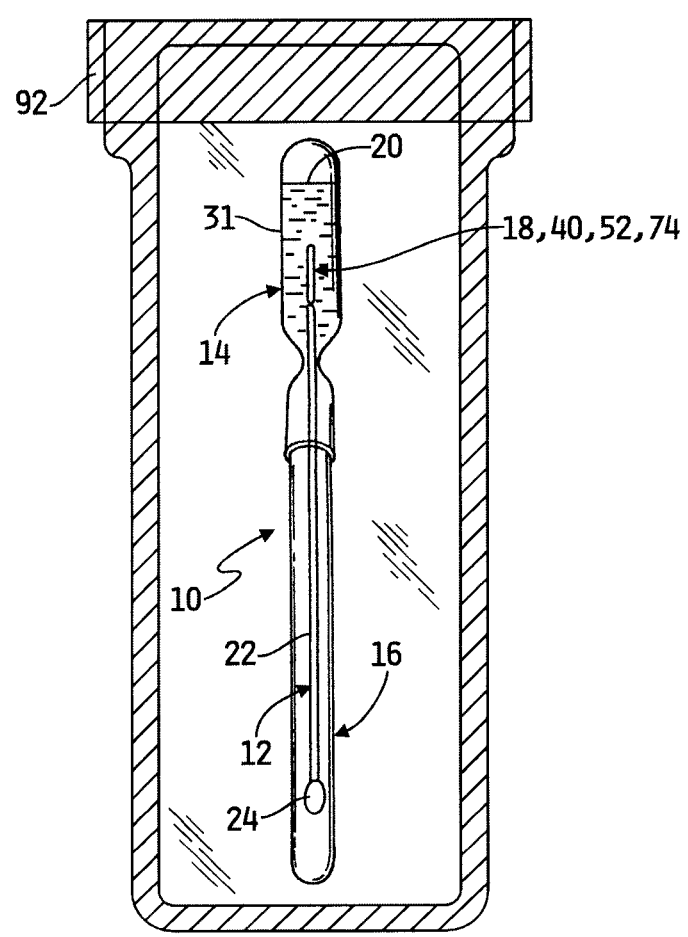
FIG. 11 is a top plan view of an illustrative specimen gathering unit including an illustrative container.
Figure 12:
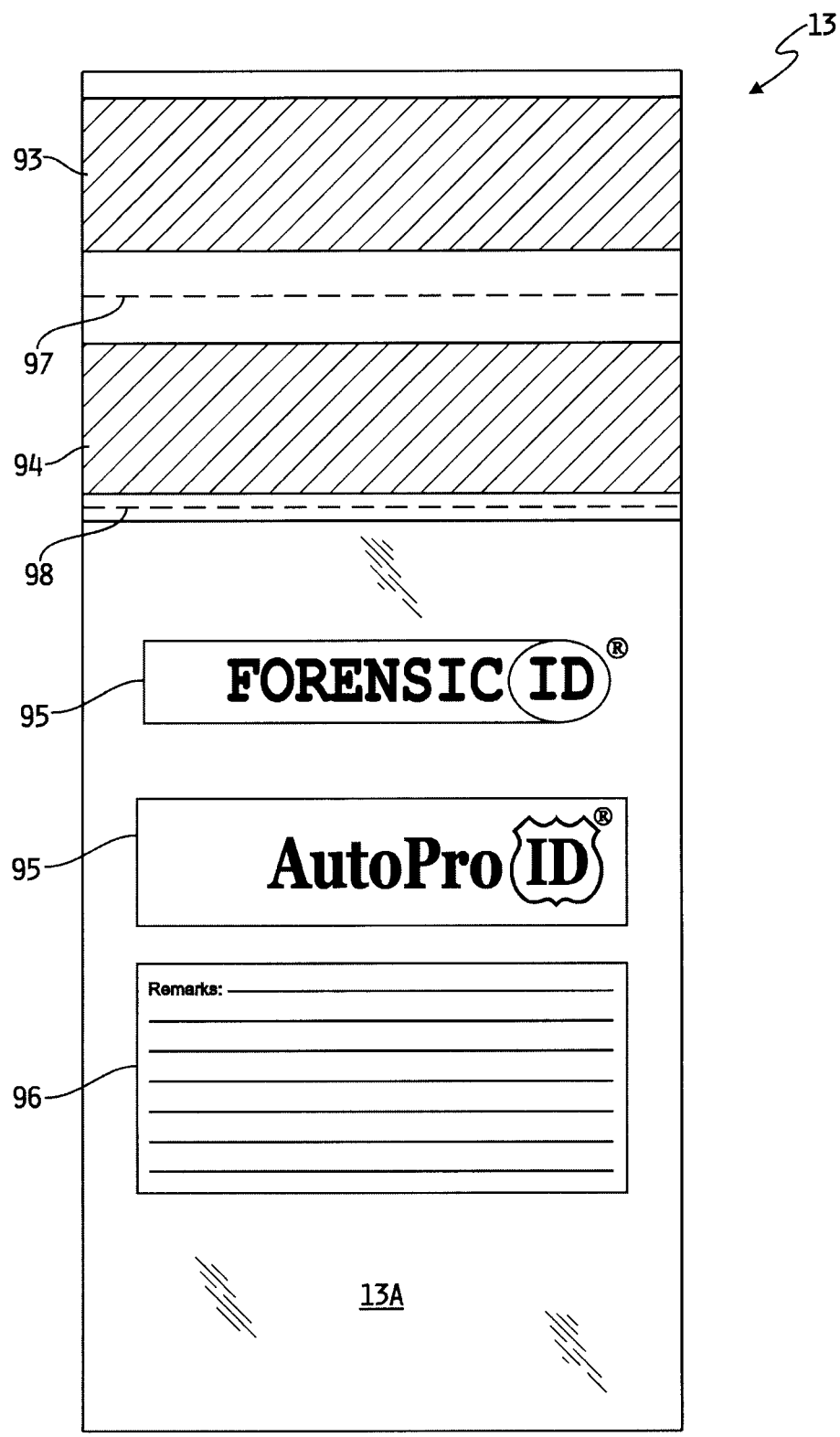
FIG. 12 is a top plan view of the obverse side of an illustrative container for use with any of the illustrative specimen gathering units.
Figure 13:
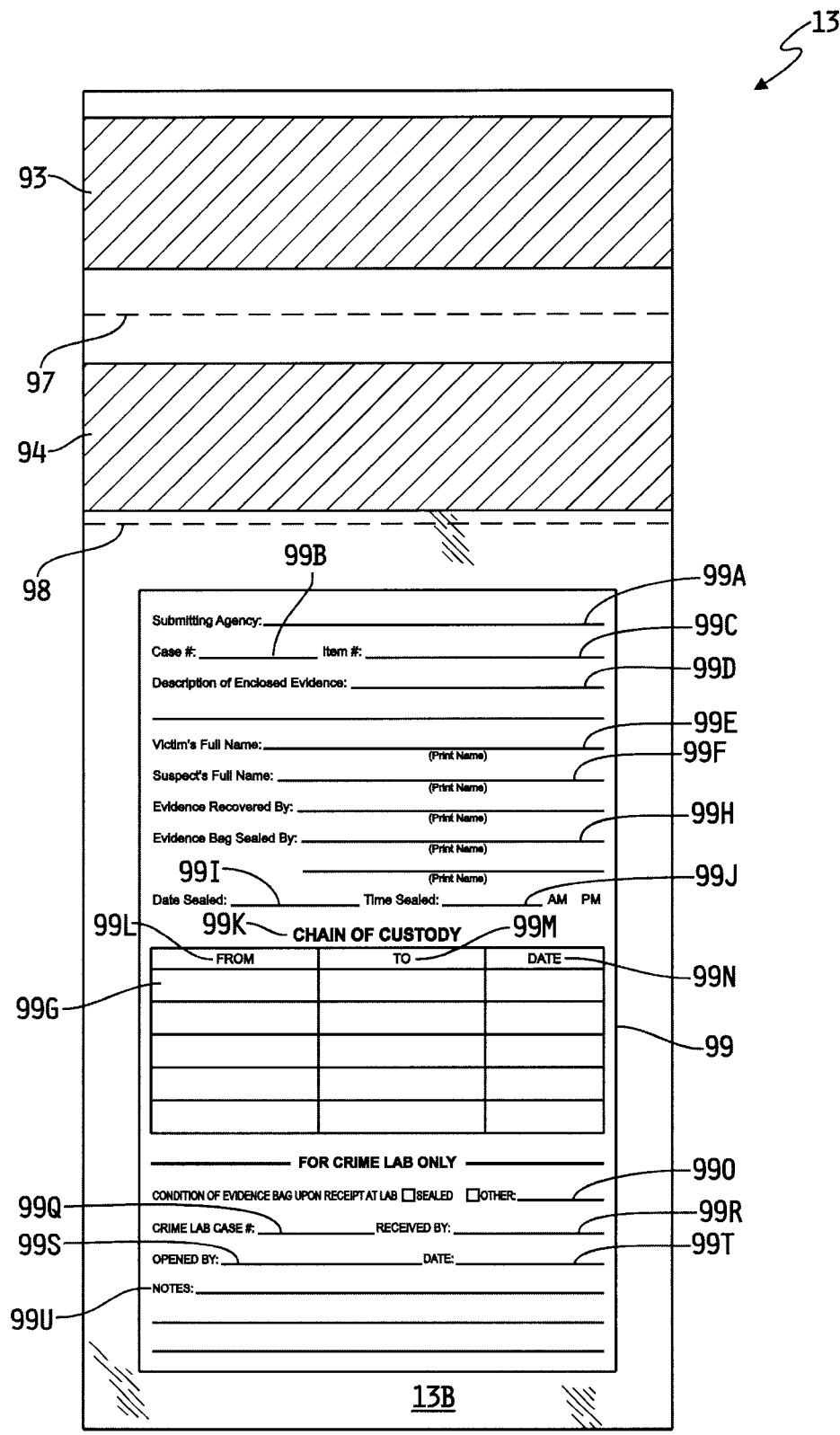
FIG. 13 is a top plan view of the reverse side of the illustrative container of FIG. 12.

Referring to FIGS. 11-13 the illustrative container(s), packaging, bag(s), or baggies 11 and 13 are depicted. Illustratively, the bag(s) 11 and 13 may be opaque, translucent, and/or transparent in whole or in any combination. The insert bag 11 illustratively comprises a sealable end having a closure or seal 92 and a closed end opposite the seal end. The seal 92 may, but need not be re-sealable. It may be sealed or sealable by any suitable means including by the use of an adhesive, heat sealing, chemical sealing, mechanical sealing and the like. It may also be provided with a perforation or other means to allow for easy opening or unsealing of the bag 11. Illustratively the insert bag 11 may have a width ranging from about 1.0 inches to about 4.0 inches. In one illustrative embodiment, the width at the seal end of the bag 11 is about 3.125 inches and the width of the internal portion at the end opposite the seal end is about 2.125 inches. The insert bag 11 illustratively may have a height of about 5.0 inches to about 12 inches. In one illustrative embodiment the height may be about 6.125 to about 7.0 inches. The seal in one illustrative embodiment has a height of about 0.750 inches and a width of about 3.125 inches. It will be appreciated that the bag 11 may be sized to accommodate both the size and the number of gathering devices 10 to be housed therein in any one kit. Similarly, the size of the evidence bag 13 may comprise any size suitable for the size and number of insert baggies 11 and specimen gathering device(s) to be carried therein. Illustratively, the evidence bag 13 comprises one or more closures or seals 93, 94. The closures may be closed or sealed by any suitable means including by the use of an adhesive, heat sealing, chemical sealing, mechanical sealing and the like. The seal(s) are illustratively but need not be resealable. In one illustrative embodiment, the kit arrives with the first seal 93 closed or sealed and the second seal 94 open or sealed. The bag 13 further illustratively comprises one or more perforations 97, 98, which illustratively aid a user in opening any closed seal 93, 94. It will be appreciated that other means may be used to aid in the opening, for example a string or ribbon may be embedded in the closure, or a notch may be fashioned in the bag 13. The second perforation 98 need not be provided if it is desired to ensure that the evidence bag is not easily opened during transportation or storage for example. Illustratively, information 95, 96, 99 may be entered on the obverse or front 13A and/or the reverse or back 13B side of the evidence bag 13. The bag 13 illustratively includes pre-formatted areas for entering the information. For example and without limitation such pre-formatted information areas and corresponding information could include one or more of the following, alone or in any combination: submitting agency or person 99A, case number 99B, item number 99C, description of the evidence 99D enclosed in the bag 13, location of the collection site 96, name of any victim(s) 99E, name of any suspect(s) 99F, name of person(s) who collected or recovered the evidence 99G, date 96 the evidence was collected, time the evidence 96 was collected, name of the person(s) 99H who sealed the bag 13, the date 99I the bag was sealed, the time 99J the bag was sealed, chain of custody information 99K detailing who the bag was transferred from 99L and to 99M and the date 99N and perhaps the time of the transfer(s), the condition of the evidence 99O upon receipt at the storage and/or analyzing organization (for example the crime lab), the case number 99Q assigned to the investigation, the name of the person 99R receiving the sealed bag 13 at the storage location and/or lab, the date and time of receipt at the storage location and/or the lab, the name of the person 99S opening the bag 13, the date 99T the bag was opened, the time the bag was opened, any notes 99U, any other remarks 96, and the like. The bag 13 may have locations and titles of one or more of the foregoing pre-printed 96, 99 on the bag. The bag 13 illustratively may have identifying information 95, for example and without limitation the name of the investigating unit or the name of the manufacturer or the like pre-printed on the bag 13. Instructions for the use of the kit may be contained within the container and/or may be printed on the container(s) itself.

Also disclosed is a method of collecting a specimen or evidence from a location such as for example and without limitation a crime scene, an automobile, a weapon, a body, a container or any other target, whether wet or dry. The collector or user should ensure that the scene is secure to avoid contamination. It will be appreciated that a user may wish to collect samples from locations other than a crime scene, for example, samples may be collected from the scene of an accident, from a grave yard, from a battlefield, from a hospital or other medical care facility; or the like. The collector may wear protective clothing, such as for example and without limitation a mask and/or gloves. The collector may remove a specimen gathering device from its packaging if any. For example and without limitation the first seal on the evidence bag may be broken and the insert bag may be removed. Illustratively, the insert bag 11 may then be unsealed and a specimen gathering device 10 may be removed. The gathering device may be charged illustratively by snapping or otherwise breaking the valve or nib in the housing base 14. Illustratively the base 14 or bulb 31 is squeezed to allow the solution 20 to empty out of the base 14 for absorption by the swab tip 24 as described herein. The housing cap or cover 16 and the housing base 14 may be separated to expose the swab tip 24. The item from which the sample is to be taken illustratively may be swabbed by the swab tip 24 to collect the sample specimen. Illustratively, the collected sample specimen may be preserved by rejoining together the housing base 14 and cover 16. The reconstituted gathering device 10 may be reinserted into the insert bag 11, which may be re-inserted into the evidence bag 13. In the alternative, the gathering device may be re-inserted into the evidence bag 13 and the insert bag 11 may be discarded. If more than one specimen gathering devices are contained in the kit, then they too may be similarly charged, used, re-constituted and re-inserted as described.

In one illustrative case of gathering a specimen from a weapon, for example a firearm such as for example a handgun, the kit illustratively may include three (3) specimen gathering devices 10. The perforation 97 may be broken to allow the insert bag with the three devices 10 to be removed. The seal 92 on the insert bag 11 is broken and one of the devices 10 is removed, charged and separated to expose the swab tip 24. Illustratively the barrel of the weapon may be swabbed by the first charged swab tip 24. Illustratively, the barrel may be swabbed vigorously, and may be swabbed on each side of the barrel 20 to 30 times with the swab tip 24. It will be appreciated that on some hand guns, for example a revolver, the generally cylindrical barrel may be swabbed all the way around, while on other hand guns, for example a clip or magazine fed gun, may have a barrel that is at least partially contained by a slide. In such a case, each side of the slide may be swabbed the illustrative 20 to 30 times. The swab tip may be protected or guarded by rejoining together the housing base 14 and cover 16 and the reconstituted device 10 may be placed in the bag 13, which may be resealed and annotated. If, the seal 94 is not designed to be un-sealed and re-sealed without breaking the seal, then it will remain open while the second device 10 is used to gather the next specimen. Illustratively, the weapon may be unloaded and made safe and the second device 10 may be used to swab the trigger, handle or grip, hammer, and back grip of the weapon in the same manner as just described. That swab may then be protected or guarded by rejoining the base 14 and cover 16 and placing it in the bag 13. The third gathering device 10 may be unsealed, charged, and used to swab the magazine, clip, or cylinder, including any exposed bullets of the weapon. The swab tip may be protected or guarded by rejoining together the base 14 and cover 16 and placing or inserting the device 10 in the bag 13. After all of the devices 10 are used, the bag 13 may be closed at the second seal or closure 94 and the bag 13 may be annotated with the relevant collection information. The specimen gathering device 10 may also be used generally as has been described to gather a DNA sample, for example a buccal swab sample, from a person, for example a victim or a suspect.

A holistic method of using and of teaching the proper use, as described herein, of the specimen gathering device 10 is also disclosed. In addition to providing background and training on the proper use of the specimen gathering device 10 and kit(s), forensic analysis, research regarding the success of the program, community education and awareness programs and media kits illustratively may be provided. This holistic approach comprises a deterrent prong, provided by the community awareness campaign, along with collection, analysis and exploitation prongs. Each of the prongs contribute to and strengthen the other prongs. For example, teaching the proper use of the device 10 leads to the successful gathering of usable specimens, which allows for analysis, which facilitates the solving of crimes (or other desired results such as identifying an abandoned item or person), which provides favorable statistics for the media campaign, which illustratively seeks to inform the public of the use and success of the device 10 in gathering even "touch" or "contact" DNA, from wet or dry surfaces, which deters future crimes.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A specimen gathering kit comprising:
    a specimen gathering device including:
        a swab member having opposing ends, wherein one end comprises a swab tip;
        a housing including a base and a cap; and
        a solution;
    wherein the housing base defines a solution chamber having a closed end and an opposite open end and wherein the solution is received within the solution chamber; and
    wherein the base and the cap are releasably joined together to house the swab member, the swab member being lodged within the cap with the end of the swab member opposite the tip extending into the solution chamber and the swab member protruding from the open end of the solution chamber;
    wherein the swab member seals the open end of the solution chamber to contain the solution therein; and
    wherein the solution comprises a buffer solution including a DNA preservative configured to gather the specimen.

2. The specimen gathering kit of claim 1 wherein the buffer solution comprises distilled water.

3. The specimen gathering kit of claim 1 further comprising Ethylenediaminetetraacetic Acid (EDTA).

4. The specimen gathering kit of claim 3 further comprising Sodium Chloride (NaCl).

5. The specimen gathering kit of claim 4 further comprising Sodium phosphate, dibasic ($Na_2HPO_4$).

6. The specimen gathering kit of claim 5 further comprising Potassium phosphate, Monobasic ($K_2HPO_4$).

7. The specimen gathering kit of claim 6 further comprising Potassium chloride (KCl).

8. The specimen gathering kit of claim 7 further comprising Glycerol.

9. The specimen gathering kit of claim 1 wherein the preservative comprises a biocide.

10. The specimen gathering kit of claim 9 wherein the biocide comprises an antimicrobial.

11. The specimen gathering kit of claim 1 wherein the opposite end of the swab is movable to unseal the solution chamber and allow the solution to flow out of the solution chamber and to come into fluid communication with the swab tip.

12. The specimen gathering kit of claim 1 further comprising an indicator that changes color upon contact with a selected material.

13. The specimen gathering kit of claim 1 wherein the specimen gathering device comprises illumination means.

14. The specimen gathering kit of claim 1 wherein the kit further comprises a container, the specimen gathering device being received within the container.

15. The specimen gathering kit of claim 14, wherein the container comprises a re-sealable bag.

16. The specimen gathering kit of claim 15, wherein the re-sealable bag comprises at least two sealing closures.

17. The specimen gathering kit of claim 16, wherein the re-sealable bag further comprises pre-formatted areas to enter information.

18. The specimen gathering kit of claim 17, wherein the kit further comprises an insert bag, the specimen gathering device being received within the insert bag, and the insert bag with the specimen gathering device therein being received within the re-sealable bag.

19. The specimen gathering kit of claim 14 further comprising instructions for collecting a specimen.

20. The specimen gathering kit of claim 14 further comprising at least two specimen gathering devices within the container.

21. A specimen gathering kit comprising:
   a specimen gathering device including:
      a swab member having opposing ends, wherein one end comprises a swab;
      a housing including a base and a cap; and
      a solution including a preservative;
   a first container sealing therein the specimen gathering device;
   a second container re-sealably sealing therein the first container containing the specimen gathering device sealed therein; and
   wherein the housing base defines a solution chamber having a closed end and an opposite open end and wherein the solution is received within the solution chamber; and
   wherein the base and the cap are releasably joined together to house the swab member, the swab member being lodged within the base with the opposite end of the swab extending into the solution chamber and the swab protruding from the open end of the solution chamber; and
   wherein the swab member initially seals the open end of the solution chamber to contain the solution therein; and
   wherein the swab member is moveable to un-seal the chamber to allow the solution to come into fluid communication with the swab.

* * * * *